United States Patent
Onda

(10) Patent No.: US 9,971,137 B2
(45) Date of Patent: May 15, 2018

(54) IMAGE GENERATION APPARATUS AND IMAGE GENERATION METHOD

(71) Applicant: CANON KABUSHIKI KAISHA, Tokyo (JP)

(72) Inventor: Suguru Onda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 162 days.

(21) Appl. No.: 15/184,563

(22) Filed: Jun. 16, 2016

(65) Prior Publication Data

US 2016/0377849 A1 Dec. 29, 2016

(30) Foreign Application Priority Data

Jun. 23, 2015 (JP) .................................. 2015-125887

(51) Int. Cl.
*H04N 7/18* (2006.01)
*G02B 21/00* (2006.01)
(Continued)

(52) U.S. Cl.
CPC .......... *G02B 21/008* (2013.01); *A61B 3/0025* (2013.01); *A61B 3/1015* (2013.01);
(Continued)

(58) Field of Classification Search
CPC ........ H04N 7/18; G02B 21/00; G02B 21/008; G02B 21/0028; G02B 21/0036; G02B 21/0072; A16B 3/0025; A16B 3/1015; A16B 3/1025; A16B 3/113; A16B 3/1225
USPC .................................... 348/78, 607; 358/296
See application file for complete search history.

(56) References Cited

U.S. PATENT DOCUMENTS 4,742,363 A * 5/1988 Shiraishi ............... G06K 15/128
347/246

5,373,518 A * 12/1994 Uchiyama .......... G06K 15/1214
372/26
(Continued)

FOREIGN PATENT DOCUMENTS

JP 2000-39560 A 2/2000
JP 2014-68703 A 4/2014

OTHER PUBLICATIONS

Sulai, Y., et al., "Visualization of retinal vascular structure and perfusion with a nonconfocal adaptive optics scanning light ophthalmoscope", J. Opt. Soc. Am. A., Mar. 2014, pp. 569-579, vol. 31, No. 3.

(Continued)

*Primary Examiner* — Trang U Tran
(74) *Attorney, Agent, or Firm* — Canon USA Inc., IP Division

(57) ABSTRACT

A processor extracts a reference signal of a scanner included in an adaptive optics SLO apparatus output while the scanner performs reciprocating scanning on a region of an eye to be inspected, generates sampling data strings of reciprocating scanning for individual imaging units included in the adaptive optics SLO apparatus using the reference signal as a sampling reference position, and compares, among the sampling data strings of the reciprocating scanning, a sampling data string of forward scanning with a sampling data string of backward scanning so as to evaluate the correlation between the sampling data strings, compares evaluation results obtained for the individual imaging units so as to evaluate reliability, and compensates a sampling reference position based on the evaluation results. An image construction unit assembles image data to construct an image of the region of the eye based on the compensated sampling reference position for each imaging unit.

20 Claims, 6 Drawing Sheets

(51) Int. Cl.
*A61B 3/00* (2006.01)
*A61B 3/10* (2006.01)
*A61B 3/12* (2006.01)
*A61B 3/113* (2006.01)

(52) U.S. Cl.
CPC .......... *A61B 3/1025* (2013.01); *A61B 3/1225* (2013.01); *G02B 21/0028* (2013.01); *G02B 21/0036* (2013.01); *G02B 21/0072* (2013.01); *H04N 7/18* (2013.01); *A61B 3/113* (2013.01)

(56) References Cited

U.S. PATENT DOCUMENTS

| | | | | |
|---|---|---|---|---|
| 5,463,410 | A * | 10/1995 | Uchiyama | B41J 2/471 347/133 |
| 6,222,580 | B1 * | 4/2001 | Yamada | G02B 26/127 347/132 |
| 7,382,929 | B2 * | 6/2008 | Cooper | H04N 1/409 348/607 |
| 8,400,698 | B2 * | 3/2013 | Fujii | G02B 26/0833 347/247 |
| 8,547,606 | B2 * | 10/2013 | Matsuo | H04N 1/047 358/474 |

OTHER PUBLICATIONS

Scoles, D., et al., "In Vivo Imaging of Human Cone Photoreceptor Inner Segments", IOVS, 2014, pp. 4244-4251, vol. 55, No. 7.

* cited by examiner

IMAGE GENERATION APPARATUS AND IMAGE GENERATION METHOD

BACKGROUND OF THE INVENTION

Field of the Invention

The present invention generally relates to ophthalmologic imaging, and in particular it relates to an image generation apparatus which generates an image of a certain region of an eye and a method for processing such image.

Description of Related Art

Inspection of a fundus of an eye is widely performed for early diagnosis of lifestyle-related diseases that are causes of blindness. A scanning laser opthalmoscope (SLO) is an ophthalmic apparatus utilizing a confocal laser microscope principle. The SLO apparatus performs high-speed raster scan on a fundus of an eye to be inspected, by using laser which is measurement light, and obtains a fundus image of high resolution which is a plane image from intensity of return light.

In recent years, an adaptive optics SLO (AO-SLO) apparatus has been developed. The OA-SLO apparatus includes an adaptive optics system which measures aberration of an eye to be inspected, in real time, by using a wavefront sensor, and compensates the aberration of measurement light and return light which occurs in the eye to be inspected, by using a wavefront compensation device. This adaptive optics SLO apparatus is capable of obtaining a plane image of high transverse resolution (hereinafter referred to as an "AO-SLO image" where appropriate).

Furthermore, in recent years, a method for observing a nonconfocal image generated based on scattering light obtained by changing a diameter, a shape, or a position of a pinhole formed in front of a light receiving unit has been used. An example is disclosed by, Sulai, Dubra et al.; "Visualization of retinal vascular structure and perfusion with a nonconfocal adaptive optics scanning light opthalmoscope", J. Opt. Soc. Am. A, Vol. 31, No. 3, pp. 569-579, 2014. It is reported that, in the nonconfocal image obtained by this method, a structure of a fundus of an eye to be inspected may be identified in a region which is not resolved by the adaptive optics SLO apparatus (refer to Scoles, Dubra et al.; "In vivo Imaging of Human Cone Photoreceptor Inner Segments", IOVS, Vol. 55, No. 7, pp. 4244-4251, 2014). Accordingly, in recent years, there has been an increase of interest in apparatuses which simultaneously obtain a confocal image and a nonconfocal image.

Such an apparatus which simultaneously obtain a confocal image and a nonconfocal image performs 2D scanning using measurement light from a resonant scanner or a galvanoscanner. Furthermore, a control circuit of such a scanner, for example, generates a synchronizing signal for image generation in synchronization with the optical scanning of the scanner so as to generate an image from a detection signal detected by a photodetector. Then, a fundus image is formed by matching (synchronizing) the signal indicating an optical scanning position of the scanner and an electric sampling position of the photodetector.

However, due to fluctuation of frequency of the resonant scanner, time delay of an electric circuit system, or the like, an optical scanning position of the scanner obtained from the synchronizing signal tends to mismatch the electric sampling position of the photodetector. Furthermore, since the adaptive optics SLO has high resolution, a difference between the optical scanning position of the scanner and the electric sampling position of the photodetector considerably affects the adaptive optics SLO. Accordingly, a large positional shift occurs between images of consecutive scan lines which are sampled in accordance with the synchronizing signal, and accordingly degradation of image quality, such as distortion of an image, tends to occur.

To address these disadvantages, Japanese Patent Laid-Open No. 2000-39560 discloses a method for obtaining or controlling an accurate position of scanning of the scanner using a dedicated hardware configuration. Furthermore, Japanese Patent Laid-Open No. 2014-68703 discloses a method for capturing a chart image for image compensation before imaging, obtaining distortion of an image from the captured image in advance, and compensating the distortion by an image process.

As resolution of an AO-SLO image becomes higher, an angle of view becomes large, and a frame rate becomes higher, a positional shift between images of consecutive scan lines becomes more relevant even if a shift between the optical scanning position and the electric sampling position is considerably small. In this case, even if the hardware configuration for detecting a scanner position is employed, as disclosed in Japanese Patent Laid-Open No. 2000-39560, it becomes considerably more difficult to detect a small shift between the optical scanning position and the electric sampling position with high accuracy and appropriate responsivity.

Furthermore, as for the shift between the optical scanning position and the electric sampling position, an amount of the shift may be changed in each imaging since the shift is affected by temperature in the apparatus, instability of a power source, and the like. Therefore, as described in Japanese Patent Laid-Open No. 2014-68703, even if distortion compensation is performed by image processing by obtaining a chart image for image compensation before image capturing so that image distortion is obtained in advance, distortion occurs in a captured image again and degradation of image quality occurs. In particular, in the case of ophthalmic apparatuses, it is difficult to simultaneously capture a chart image for image compensation and a fundus image using measurement light from the single resonant scanner in terms of a configuration of the apparatus, and therefore, it is difficult to compensate entire distortion in an image using the method disclosed in Japanese Patent Laid-Open No. 2014-68703.

Specifically, in general techniques, it is difficult to obtain an image in which distortion thereof caused by characteristics of a scanner is compensated without using a special hardware configuration, a chart image for compensation, or the like.

SUMMARY OF THE INVENTION

The present invention provides an image generation apparatus and an image generation method capable of obtaining an image in which distortion thereof caused by characteristics of a scanner is compensated without using a special hardware configuration, a chart image for compensation, or the like.

According to an aspect of the present invention, an image generation apparatus is connected to an ophthalmic apparatus including a plurality of imaging units each of which has a photoelectric conversion unit which receives return light of measurement light used by a scanner to scan a region of an eye to be inspected and converts the return light into an electric signal. The image generation apparatus includes an extraction unit configured to extract a reference signal of the scanner obtained while the scanner performs reciprocating scanning once, a data string generation unit configured to generate sampling data strings of reciprocating scanning based on the electric signals for individual imaging units using the reference signal as a sampling reference position, a first evaluation unit configured to compare, among the sampling data strings of the reciprocating scanning, a sampling data string of forward scanning with a sampling data string of backward scanning so as to evaluate the correlation between the sampling data strings, a second evaluation unit configured to compare first evaluation results of the individual imaging units obtained as results of the evaluation performed by the first evaluation unit so as to evaluate reliability, a reference position compensation unit configured to compensate the sampling reference position in accordance with the first evaluation results and a second evaluation result obtained as a result of the evaluation performed by the second evaluation unit, and an image construction unit configured to assemble image data to construct an image of the region of the eye based on the sampling data strings of the reciprocating scanning for each imaging unit in accordance with the sampling reference position compensated by the reference position compensation unit.

Further features of the present invention will become apparent from the following description of exemplary embodiments with reference to the attached drawings.

DESCRIPTION OF THE EMBODIMENTS

Hereinafter, an embodiment of the present invention will be described with reference to the accompanying drawings.

In the embodiment of the present invention, a case where, when an image of a retina (a fundus) is captured as a certain region of an eye to be inspected by an adaptive optics SLO apparatus, the image is configured based on a signal value obtained by scanning performed on the certain region using a resonant scanner and a galvanoscanner will be described.

Specifically, in this embodiment, a confocal image and a nonconfocal image are simultaneously captured using a plurality of imaging units, and image distortion is compensated by an image process using sampling data strings obtained by sampling. In the same scanning position, sampling positional shift amounts of the confocal image and the nonconfocal image are the same as each other. However, features of the images are different from each other, and therefore, different compensation results may be obtained when compensation of individual sampling reference positions of the images is performed. In this embodiment, false detection of distortion compensation may be reduced by comparing reliabilities after the compensation. In this embodiment, by generating image data using a compensated sampling reference position, an image of a retina (a fundus image) in which image distortion caused by characteristics of a scanner (a resonant scanner in this embodiment) is compensated may be obtained without using a special hardware configuration, a chart image for image compensation, or the like.

Schematic Configuration of Image Generation Apparatus

Figure 1:
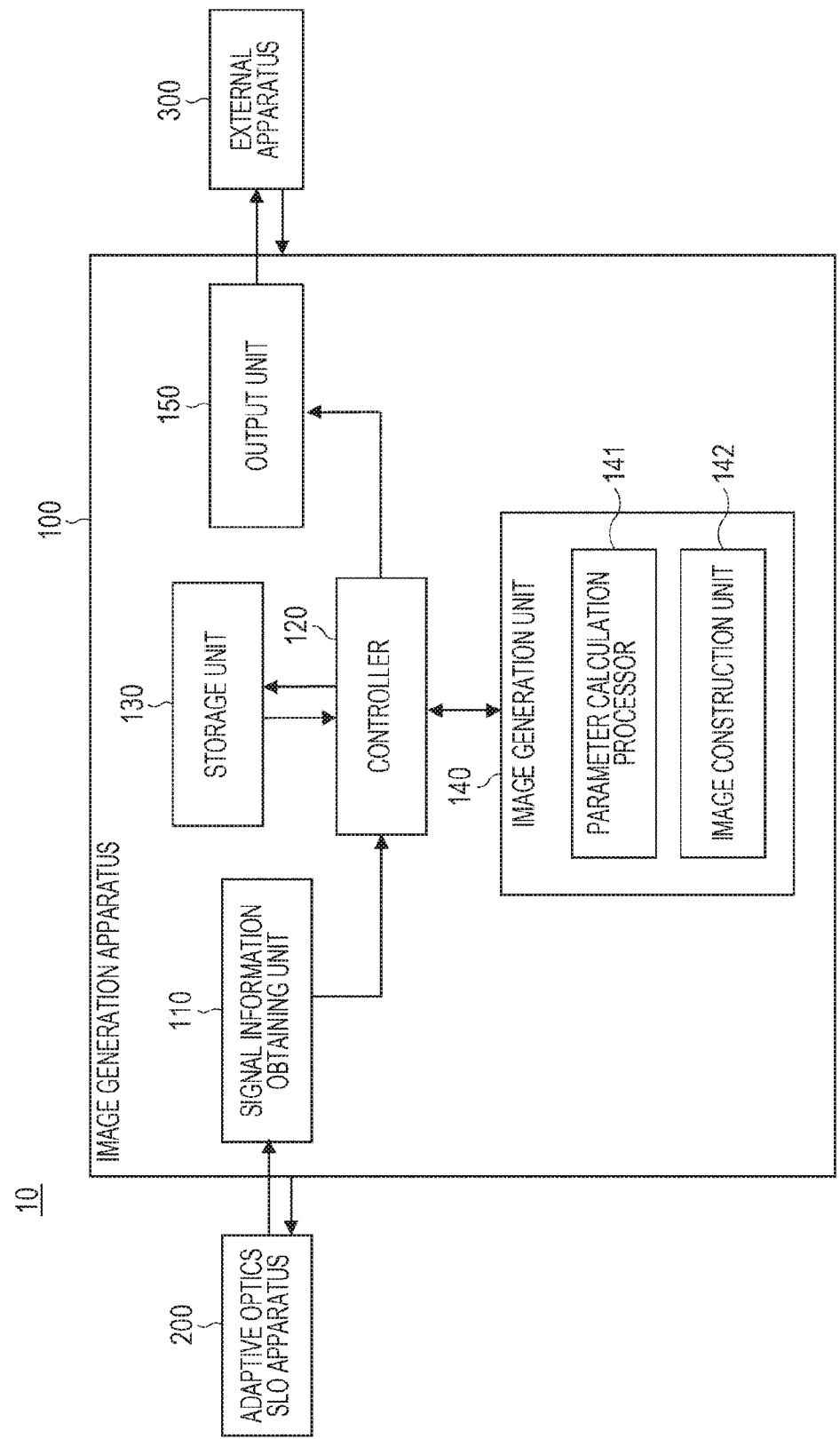
FIG. 1 is a block diagram schematically illustrating a configuration of an image generation system including an image generation apparatus according to an embodiment of the present invention.

FIG. 1 is a block diagram schematically illustrating a configuration of an image generation system 10 including an image generation apparatus 100 according to this embodiment of the present invention.

The image generation system 10 includes the image generation apparatus 100, an adaptive optics SLO apparatus 200, and an external apparatus 300 as illustrated in FIG. 1.

The adaptive optics SLO apparatus 200 (an ophthalmic apparatus) includes a plurality of imaging units each of which includes a photoelectric conversion unit which receives return light of measurement light used for reciprocating scanning performed by a scanner on a certain region of an eye to be inspected and converts the return light into an electric signal. The image generation apparatus 100 is connected to the adaptive optics SLO apparatus 200 in a communication available manner. The image generation apparatus 100 includes a signal information obtaining unit 110, a controller 120, a storage unit 130, an image generation unit 140, and an output unit 150 as illustrated in FIG. 1.

The signal information obtaining unit 110 obtains trigger signals of a resonant scanner and a galvanoscanner, and signal information such as a signal of reflection from a retina of the eye to be inspected, from the adaptive optics SLO apparatus 200. Here, the trigger signal is a reference signal indicating that the resonant scanner and the galvanoscanner are in specific positions (reference positions). The signal information obtained by the signal information obtaining unit 110 is stored in the storage unit 130 through the controller 120.

The controller 120 integrally controls operations of the units of the image generation apparatus 100.

The storage unit 130 stores the signal information obtained by the signal information obtaining unit 110, various information required for a process to be performed by the image generation apparatus 100, various information (including various image data) obtained in the process performed by the image generation apparatus 100, and the like.

The image generation unit 140 performs generation of various image data, and as illustrated in FIG. 1, the image generation unit 140 includes a parameter calculation processor 141 and an image construction unit 142.

The parameter calculation processor 141 extracts the trigger signals (the reference signals) of the galvanoscanner and the resonant scanner in accordance with the signal information obtained by the signal information obtaining unit 110. Specifically, in this embodiment, reference signals of the scanners output while the scanners perform reciprocating scanning once are extracted. The parameter calculation processor 141 which performs the extraction of the reference signals constitutes an extraction unit. Subsequently, the parameter calculation processor 141 generates sampling data strings corresponding to reciprocating scanning based on reflection signals (electric signals obtained by photoelectric conversion units of the adaptive optics SLO apparatus 200) for individual imaging units included in the adaptive optics SLO apparatus 200 using the extracted trigger signals (the reference signals) as sampling reference positions. The parameter calculation processor 141 which generates the sampling data strings constitutes a data string generation unit. Then the parameter calculation processor 141 compares sampling data strings corresponding to forward scanning with sampling data strings corresponding to backward scanning in the generated sampling data strings of the reciprocating scanning and evaluates the correlations between the sampling data strings for individual imaging units. The parameter calculation processor 141 which evaluates the correlations constitutes a first evaluation unit. Thereafter, the parameter calculation processor 141 compares first evaluation results of the individual imaging units obtained as results of the evaluation of the correlations described above so as to evaluate reliability. The parameter calculation processor 141 which evaluates the reliability constitutes a second evaluation unit. Subsequently, the parameter calculation processor 141 compensates the sampling reference positions described above in accordance with the first evaluation results and a second evaluation result obtained as a result of the evaluation of the reliability described above. The parameter calculation processor 141 which compensates the sampling reference position constitutes a reference position compensation unit.

The image construction unit 142 assembles image data to construct (form) an image of the retina of the eye to be inspected in accordance with the sampling data strings of the reciprocating scanning described above for individual imaging units in accordance with the sampling reference positions compensated by the parameter calculation processor 141.

The output unit 150 outputs the image data generated by the image generation unit 140 and the various information and the like stored in the storage unit 130 to the external apparatus 300.

The adaptive optics SLO apparatus 200 further includes an adaptive optics system which compensates aberration of the measurement light or the return light of the measurement light generated in the eye to be inspected.

The external apparatus 300 is connected to the image generation apparatus 100 in a communication available manner, and is an output apparatus, such as a display apparatus, or a database.

Schematic Configuration of Adaptive Optics SLO Apparatus

Next, a schematic configuration of the adaptive optics SLO apparatus 200 illustrated in FIG. 1 will be described.

Figure 2:
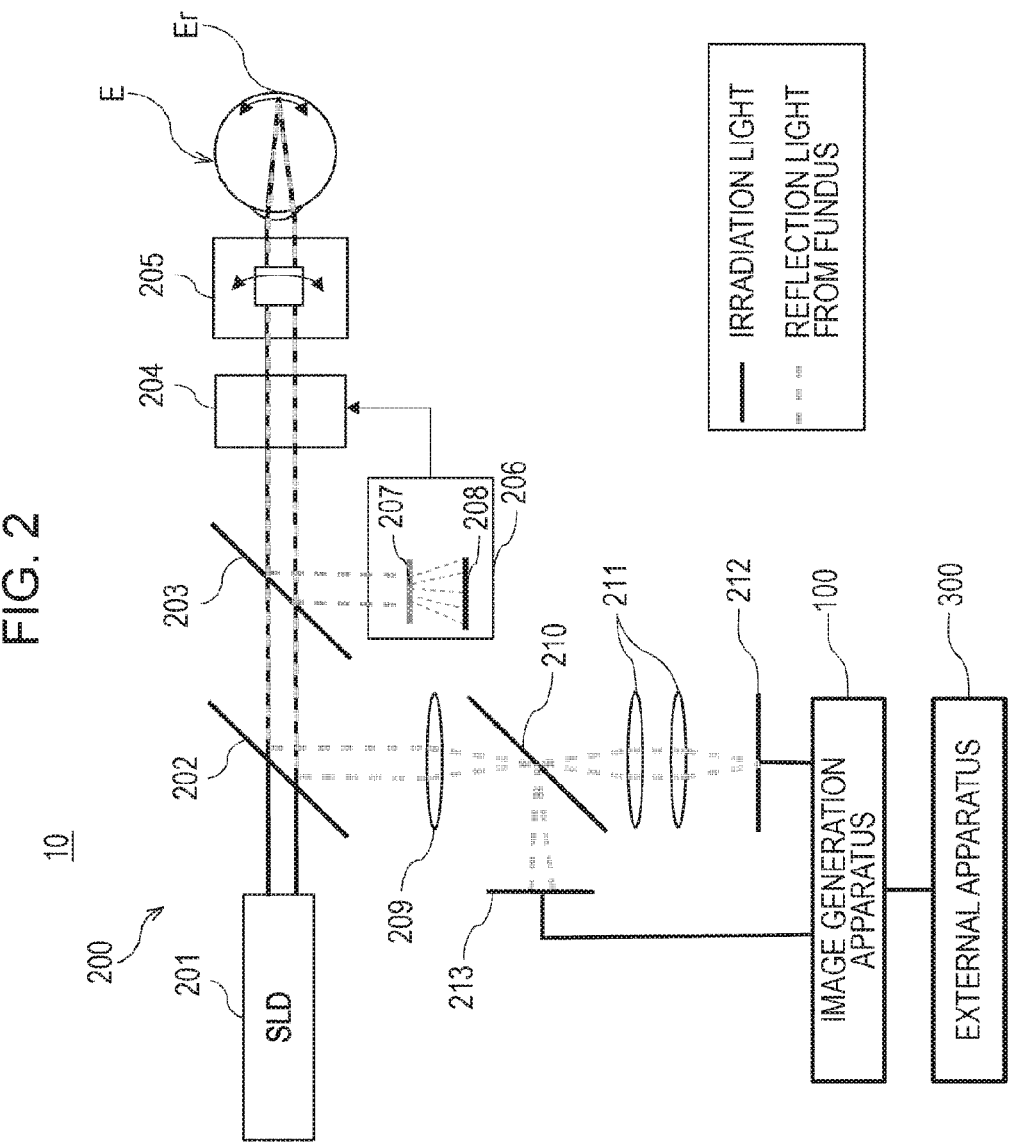
FIG. 2 is a block diagram schematically illustrating a configuration of an adaptive optics SLO apparatus illustrated in FIG. 1.

FIG. 2 is a block diagram schematically illustrating a configuration of the adaptive optics SLO apparatus 200 illustrated in FIG. 1. In addition to the schematic configuration of the adaptive optics SLO apparatus 200 illustrated in FIG. 1, the image generation apparatus 100 and the external apparatus 300 illustrated in FIG. 1 are also illustrated in FIG. 2.

As illustrated in FIG. 2, the adaptive optics SLO apparatus 200 includes a super luminescent diode (SLD) 201, beam splitters 202 and 203, an adaptive optics system 204, an X-Y scanning mirror 205, a Shack-Hartmann wavefront sensor 206, focus lenses 209 and 211, an annular mirror 210, and photosensors 212 and 213.

Light emitted from the SLD 201 serving as a light source is reflected by a fundus of a retina Er of an eye E to be inspected, a portion of the reflection light is guided to the Shack-Hartmann wavefront sensor 206 through the beam splitter 203, and the other portion of the reflection light is guided to the photosensors 212 and 213 through the beam splitter 202.

The Shack-Hartmann wavefront sensor 206 is used to measure aberration of the eye to be inspected E and includes a CCD sensor 208 and a lens array 207 disposed in front of the CCD sensor 208. In the Shack-Hartmann wavefront sensor 206, when incident light passes the lens array 207, a group of bright spots is projected on the CCD sensor 208 and wave aberration is measured in accordance with positional shifts among the projected bright spots.

The adaptive optics system 204 compensates the aberration by driving an aberration compensation device (not shown) in accordance with the wave aberration measured by the Shack-Hartmann wavefront sensor 206. Examples of the aberration compensation device include a deformable mirror and a spatial light phase modulator. The light which has been subjected to the aberration compensation is transmitted through the beam splitters 203 and 202, the focus lens 209, and the annular mirror 210, and confocal light is guided to the photosensor 213 serving as a first photoelectric conversion unit and nonconfocal light is guided to the photosensor 212 serving as a second photoelectric conversion unit through the focus lens 211. The light beams guided to the photosensor 212 and the photosensor 213 are converted into electric signals in the photosensors 212 and 213.

Here, in the example of FIG. 2, a confocal imaging unit is constituted by the components 201 to 206 and the components 209, 210, and 213 and a nonconfocal imaging unit is constituted by the components 201 to 206 and the components 209 to 212.

Here, the annular mirror 210 has a mask which reflects confocal light and which allows nonconfocal light to pass. Here, as disclosed in Sulai, Dubra et al.; "Visualization of retinal vascular structure and perfusion with a nonconfocal adaptive optics scanning light opthalmoscope", J. Opt. Soc. Am. A, Vol. 31, No. 3, pp. 569-579, 2014, for example, nonconfocal light may be divided in an arbitrary direction and a photosensor may be additionally provided so that nonconfocal light beams obtained by the division in the arbitrary direction are received by the photosensor 212 and the added photosensor. Although only one photosensor 212 receives nonconfocal light for simplicity of description in this embodiment, the present invention is not limited to this and a plurality of photosensors may be provided for detecting the nonconfocal light. Specifically, when this configuration is generalized for description, the plurality of imaging units included in the adaptive optics SLO apparatus 200 correspond to the confocal imaging unit which detects confocal light and at least one nonconfocal imaging unit which detects at least one nonconfocal light beam.

By driving the X-Y scanning mirror 205, a scanning position on the fundus Er of the eye to be inspected E may be controlled and information on an imaging target region and time (the number of frames/a frame rate) specified by an imaging practitioner in advance may be obtained. The X-Y scanning mirror 205 includes a resonant scanner in an X direction which is a main scanning direction and a galvanoscanner in a Y direction which is a sub-scanning direction. Signal information of the X-Y scanning mirror 205 is transmitted to the image generation apparatus 100 and is used when the image generation apparatus 100 generates image data (moving-image data or still-image data). Although the signal information is obtained in forward scanning and backward scanning which are main scanning of the resonant scanner in this embodiment, the present invention is not limited to this.

To focus a specific depth position on the fundus Er of the eye to be inspected E, adjustment using the aberration compensation device included in the adaptive optics system 204 or adjustment by moving a focus adjustment lens (not illustrated) disposed in an optical system may be employed.

Furthermore, a movement of the eye to be inspected E may be tracked (tracking) so that influence of an involuntary movement of an eye referred to as an "involuntary eye movement", an eye movement caused by defect of visual fixation, or a movement of the eye to be inspected E caused by a movement of a face is reduced. In this case, measurement of a movement of the fundus Er is performed by pattern matching in which a template image which is an image of a small region having a feature is extracted from a generated fundus image and a portion which is the most similar to the template image is retrieved from a newly generated fundus image, or the like. Here, the controller 120 of the image generation apparatus 100 performs control for tracking the movement of the eye to be inspected E and compensating an imaging position, for example. The controller 120 which performs the control for compensating the imaging position constitutes a compensation control unit. Then the adaptive optics SLO apparatus 200 compensates the imaging position by tracking the eye to be inspected E in accordance with the compensation control performed by the controller 120 of the image generation apparatus 100. Specifically, a scanner, not illustrated, is disposed in the optical system of the adaptive optics SLO apparatus 200 and a position of irradiation light follows the movement of the fundus Er by the scanner.

Procedure of Process of Image Generation Apparatus

Next, a procedure of a process performed by the image generation apparatus 100 according to this embodiment of the present invention will be described.

Figure 3:
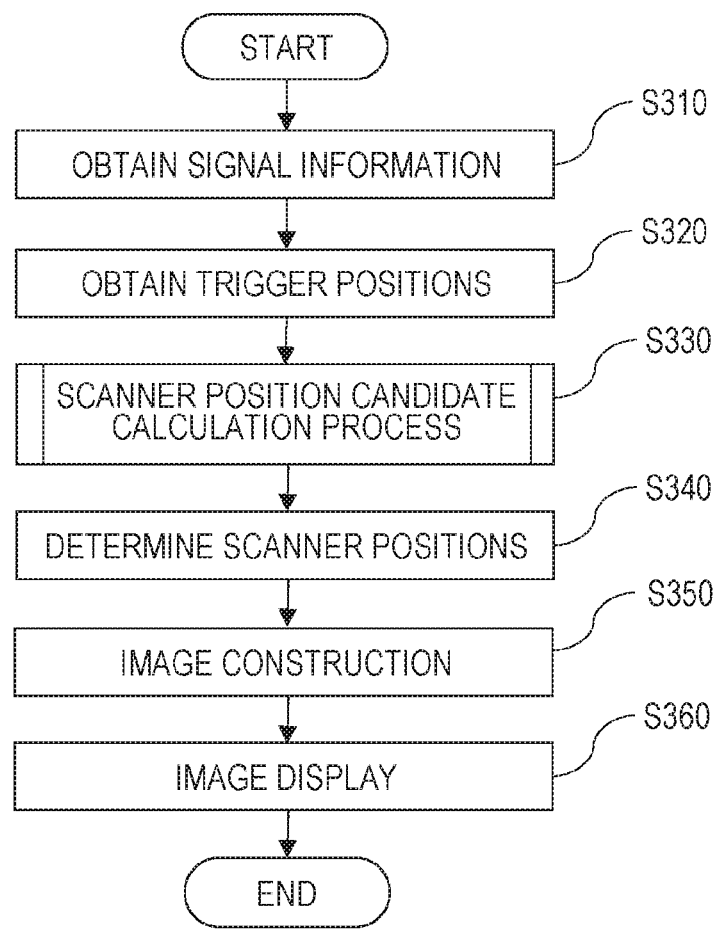
FIG. 3 is a flowchart illustrating a procedure of a process performed by the image generation apparatus according to the embodiment of the present invention.

FIG. 3 is a flowchart illustrating a procedure of a process performed by the image generation apparatus 100 according to the embodiment of the present invention.

Step S310

First, in step S310, the signal information obtaining unit 110 obtains signal information for at least one image obtained by the adaptive optics SLO apparatus 200. The signal information to be obtained includes four signal information items, that is, a trigger signal of the galvanoscanner and a trigger signal of the resonant scanner which are used for imaging of the retina of the eye to be inspected E, and a confocal reflection signal and a nonconfocal reflection signal which are reflected by the retina of the eye to be inspected E obtained by the imaging. The signal information obtained in step S310 is stored in the storage unit 130 through the controller 120. Furthermore, hardware control information associated with the obtained signal information is also obtained and is stored in the storage unit 130 through the controller 120. Here, the control information indicates information on a frame rate corresponding to a sampling frequency and a frequency of the galvanoscanner at a time when the reflection signal reflected by the retina of the eye to be inspected E is obtained. The control information may be included in an imaging information file added to the signal information or included as tag information of the signal information.

Step S320

Subsequently, in step S320, the parameter calculation processor 141 extracts the trigger signals (the reference signals) of the galvanoscanner and the resonant scanner from the signal information stored in the storage unit 130 so as to obtain trigger positions. Here, the trigger positions serve as references for obtaining pixel values by sampling the reflection signals (the sampling reference positions). Furthermore, the parameter calculation processor 141 stores the obtained trigger position information in the storage unit 130 through the controller 120.

Figure 5:
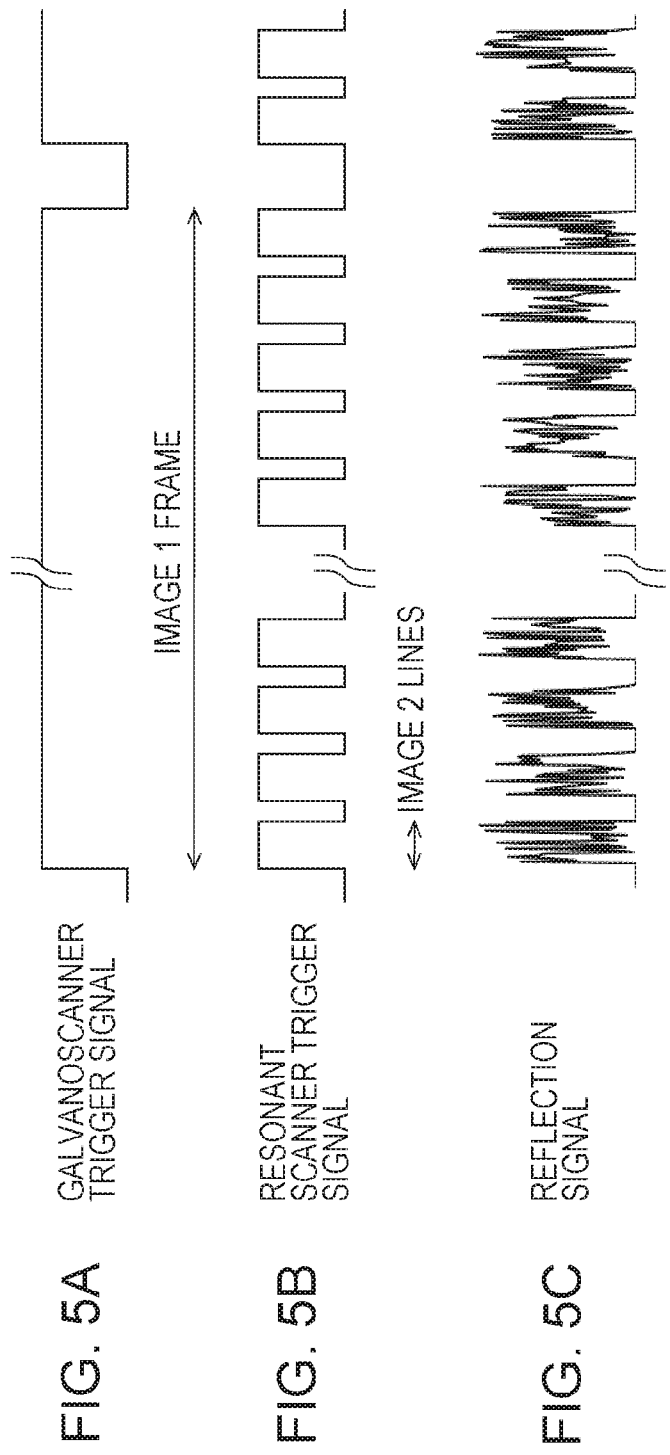
FIGS. 5A to 5C are diagrams illustrating a time chart of a trigger signal of a galvanoscanner, a time chart of a trigger signal of a resonant scanner, and a time chart of a reflection signal, respectively.

FIGS. 5A to 5C are diagrams illustrating a time chart of the trigger signal of the galvanoscanner, a time chart of the trigger signal of the resonant scanner, and a time chart of the reflection signal, respectively, according to this embodiment of the present invention.

The trigger signals of the galvanoscanner and the resonant scanner have characteristics as illustrated in FIGS. 5A and 5B, respectively, and therefore, the parameter calculation processor 141 performs extraction of the trigger signals by threshold processing. Specifically, the parameter calculation processor 141 detects and extracts a trigger signal when change of signal intensity becomes equal to or larger than a certain threshold value.

The galvanoscanner performs scanning once in a horizontal direction of an image while one trigger signal is detected and meanwhile an image is captured. The resonant scanner performs scanning for two lines (forward scanning and backward scanning) in a vertical direction of the image while one trigger signal is detected and meanwhile two lines of forward scanning and backward scanning in the vertical direction of the image are captured. Therefore, the parameter calculation processor 141 extracts a timing of start of detection of a trigger signal as a trigger position, that is, a sampling reference position.

Furthermore, the reflection signal illustrated in FIG. 5C has a value obtained by detecting intensity of reflection light from the fundus Er of the eye to be inspected E using the photosensor 212 or the photosensor 213 illustrated in FIG. 2. As illustrated in FIG. 5B, sampling is performed only while the trigger signal of the resonant scanner is detected, and signal information in this period is used for generation of an image.

In this embodiment, the sampling may be consecutively performed while the resonant scanner performs scanning, but the present invention is not limited to this. Furthermore, various methods may be employed as a method for obtaining a trigger position other than the method employed in this embodiment.

Step S330

Next, in step S330, the parameter calculation processor 141 generates sampling data string for reciprocating scanning based on the reflection signal of each of the plurality of imaging units (the confocal imaging unit and the nonconfocal imaging unit) in accordance with the trigger position obtained in step S320. Then the parameter calculation processor 141 calculates a candidate of a scanner position (sampling reference position) at a time of outputting the trigger signal using the generated sampling data string for individual imaging units. Then the parameter calculation processor 141 stores the calculated scanner position candidate information in the storage unit 130 through the controller 120.

Figure 4:
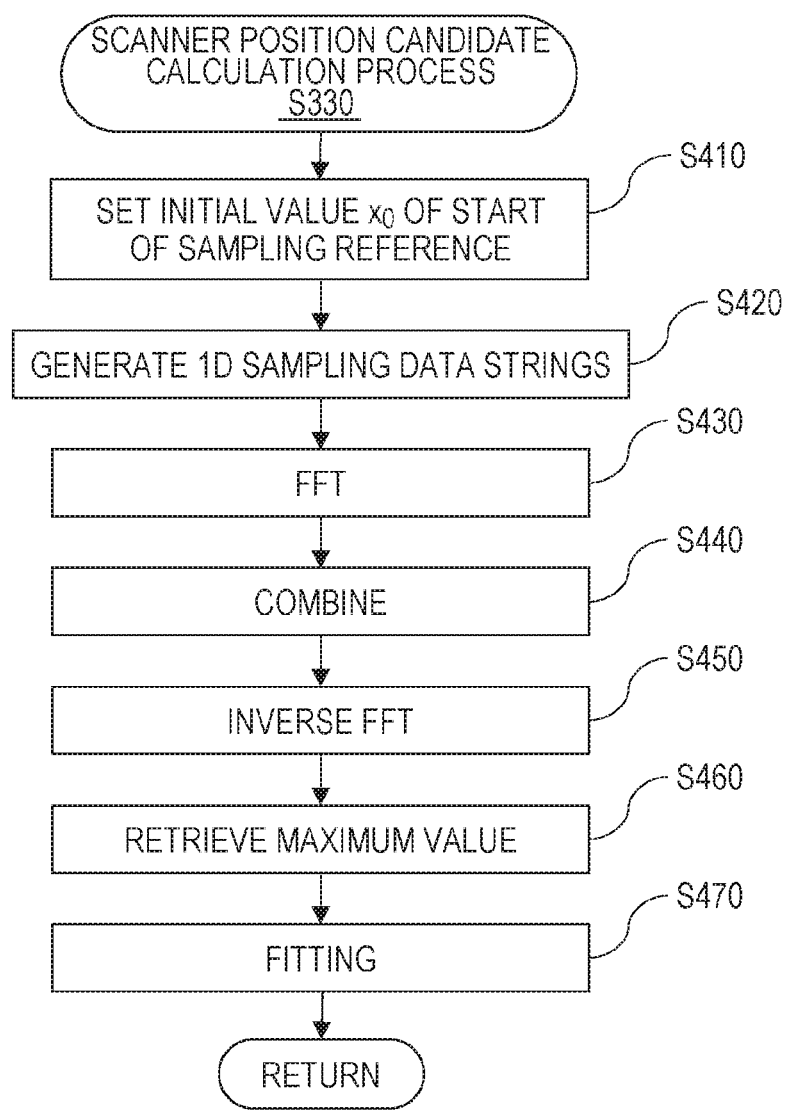
FIG. 4 is a flowchart illustrating a procedure of a scanner position candidate calculation process in step S330 of FIG. 3 in detail.

FIG. 4 is a flowchart illustrating a procedure of the scanner position candidate calculation process in step S330 of FIG. 3 in detail. Here, in a description below, the scanner position candidate calculation process is performed for each reciprocating scanning operation (one forward and backward scanning) of the resonant scanner on each of a plurality of images consecutively captured by the confocal imaging unit and the nonconfocal imaging unit, and the scanner position candidate calculation process is repeatedly performed the number of times corresponding to a number of reciprocating scanning operations performed on one image, and this process is similarly performed on the plurality of images.

In the scanner position candidate calculation process of this embodiment, a sampling data string corresponding to forward scanning is compared with a sampling data string corresponding to backward scanning in sampling data strings of the reciprocating scanning using spatial frequency domain data of the sampling data string of the forward scanning and the sampling data string of the backward scanning so that the correlation between the sampling data strings is evaluated for each imaging unit. In this embodiment, the correlation is evaluated by comparing the sampling data string of the forward scanning with the sampling data string of the backward scanning by pattern matching using a spatial frequency function of a pixel which is referred to as a "cross correlation method", for example. As concrete evaluation, a process of calculating a position in which the correlation between the sampling data string of the forward scanning and the sampling data string of the backward scanning in the reciprocating scanning is the highest is performed. Note that, although the cross correlation method is used for the evaluation in the example described above, the embodiment is not limited to this, and a phase-only-correlation method which is a method for calculating the amount of misalignment of two images using only phase information obtained through Fourier transform of the images. Furthermore, in a processing step below illustrated in FIG. 4, the same calculation is performed on a confocal side and a nonconfocal side.

Step S410

First, in step S410, the parameter calculation processor 141 sets a position of the resonant scanner at a time when the trigger signal is output as an initial position $x_0$ of a sampling reference start position in accordance with the control information obtained in step S310. Here, various methods may be employed for setting the initial position $x_0$, and the initial position $x_0$ is set taking a trigger delay from a trigger position into consideration, for example, in this embodiment. Furthermore, as another method, a method for narrowing, in a case where a plurality of images are to be consecutively captured, a retrieval range of an estimation position by setting an average scanner estimation position of reciprocating scanning operations performed on images captured before the images to be captured as an initial position may be employed.

Step S420

Next, in step S420, the parameter calculation processor 141 generates a pair 1D sampling data strings corresponding to two lines for one reciprocating scanning operation of the resonant scanner for both of the confocal side and the nonconfocal side in accordance with the initial position $x_0$ of the sampling reference start position set in step S410.

Step S430

Subsequently, in step S430, the parameter calculation processor 141 generates 1D spatial domain data strings on the confocal side and the nonconfocal side by performing Fourier transform on the 1D sampling data strings for the two lines of the reciprocating scanning operation generated in step S420. Here, as a method for calculating the spatial frequency domain data, a calculation method using discrete Fourier transform may be employed, for example. In particular, a calculation method using Fast Fourier transform (FFT) is preferably employed to realize a high-speed operation. In a description below, as the method for calculating the spatial frequency domain data, the calculation method using FFT is employed, and a hann window which is a general window function is used.

Furthermore, a region on which the FFT is to be performed preferably includes a region having luminance gradient, such as a region of some sort of structure, and therefore, the region is as large as possible and includes a region in which a speed of the resonant scanner at scanning center is high. Specifically, to include the region in which the speed of the resonant scanner at the scanning center is high corresponds to performance of the evaluation described above using the sampling data strings of the reciprocating scanning in a range which is less affected by image distortion caused by scanning of the resonant scanner than other ranges.

Note that to realize higher speed calculation, only a narrower region including a region having large luminance gradient in a sampling data string may be used or an amount of calculation may be reduced by FFT using a fixed point, bit shift, or the like. As described above, the method for the calculation of the spatial frequency domain is not limited to the methods described above. Furthermore, in this embodiment, a mode in which the evaluation described above is performed on a region in which at least change of luminance gradient is large in the sampling data string of the forward scanning and the sampling data string of the backward scanning which are adjacent to each other may be employed.

Step S440

Subsequently, in step S440, the parameter calculation processor 141 combines a spatial frequency domain data string A of the sampling data string of the forward scanning generated in step S430 and a spatial frequency domain data array B of the sampling data string of the backward scanning generated in step S430 with each other in both of the confocal side and the nonconfocal side. Here, as a method for the combining, a general method used in a calculation in the cross correlation method is used, and A is multiplied by conjugation of B.

Step S450

Thereafter, in step S450, the parameter calculation processor 141 performs inverse Fourier transform on the combined image of the spatial frequency domain data strings of the sampling data strings of the reciprocating scanning on the confocal side obtained in step S440 and the combined image of the spatial frequency domain data strings of the sampling data strings of the reciprocating scanning on the nonconfocal side obtained in step S440. The inverse FFT is used also here as the inverse Fourier transform.

Step S460

Subsequently, in step S460, the parameter calculation processor 141 retrieves positions of data points having the maximum values in the inverse FFT data strings on the confocal side and the nonconfoal side obtained in step S450.

Figure 6:
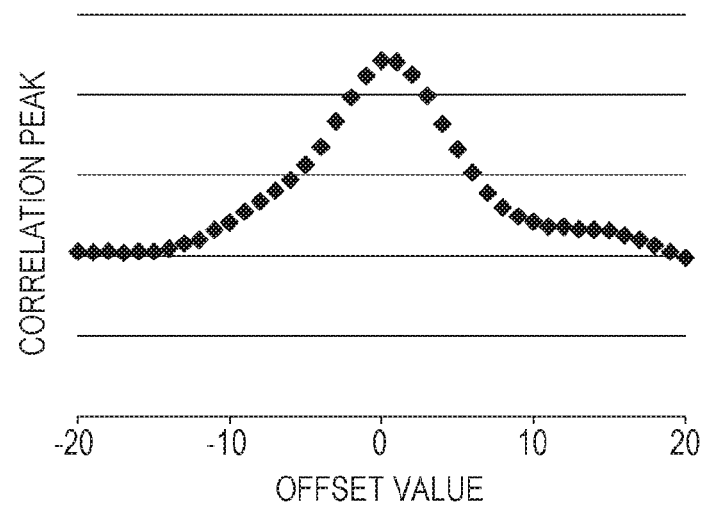
FIG. 6 is a graph illustrating inverse FFT data array obtained by an inverse FFT process in step S450 of FIG. 4.

FIG. 6 is a graph illustrating an inverse FFT data string obtained by the inverse FFT process performed in step S450 of FIG. 4. In the graph of FIG. 6, an axis of ordinates indicates a magnitude of a correlation peak, and an axis of abscissae indicates an offset value of the sampling lines in the reciprocating scanning in a scanning direction. The offset value indicates the amount of shift (offset) between the forward and backward scanning signals. According to the graph of FIG. 6, the maximum value is obtained when the offset value is 0. The 0 indicates a situation where the scanning beam scans the same area. Here, as a method for retrieving a data point having the maximum value, retrieval may be performed in a range of a physically possible minimum shift, due to events such as delay of a frequency of the resonant scanner or latency of an electric circuit, and any other method may be employed.

Since the cross correlation method is used when the evaluation described above is performed in this embodiment, a mode for retrieving the maximum value of the correlation peak may be employed, for example. Furthermore, also in a case where a phase-only-correlation method is used when the evaluation described above is performed, the maximum value of the correlation peak may be retrieved, for example.

Step S470

Then, in step S470, the parameter calculation processor 141 performs fitting on both of the confocal side and the nonconfocal side using data in the vicinity of positions of the data points on the confocal side and the nonconfocal side obtained in step S460 so as to calculate maximum peak values in inverse FFT data and offset values corresponding to the maximum peak values.

Since the cross correlation method is used when the evaluation described above is performed in this embodiment, a mode for determining a position of a correlation peak by performing arbitrary fitting in the vicinity of the maximum value of the correlation peak may be employed. Furthermore, also in a case where the phase-only-correlation method is used when the evaluation described above is performed, the mode for determining a position of a correlation peak by performing arbitrary fitting in the vicinity of the maximum value of the correlation peak may be employed.

By performing the fitting as described above, a reference position may be obtained in each sub-sampling unit. Although an arbitrary least-square method may be used for the fitting, parabola fitting employing easy calculation is used in this embodiment. In FIG. 6, by performing the parabola fitting using data in three points having offset values of −1, 0, and 1, an offset value having the highest correlation between the sampling data strings in the reciprocating scanning may be calculated in a sub-sampling unit. By taking a trajectory of the resonant scanner into consideration for the calculated offset value, a shift amount $\Delta x$ from the sampling reference start position may be calculated and "$x_0 + \Delta x$" may be determined as the compensated sampling reference position which is a position of the resonant scanner at the time when the trigger signal is output. The compensated sampling reference position information is transmitted from the parameter calculation processor 141 and stored in the storage unit 130 through the controller 120.

The scanner position candidate calculation process in step S330 of FIG. 3 is executed by performing the process from step S410 to step S470 of FIG. 4. Here, FIG. 3 is referred to again.

Step S340

After the process in step S330 of FIG. 3 is terminated according to the algorithmic flow of FIG. 4, the process proceeds to step S340.

In step S340, the parameter calculation processor 141 determines one scanner position to be compensated in candidates of a scanner position (a sampling reference position) in each reciprocating scanning operation calculated in step S330. Here, in this embodiment, the parameter calculation processor 141 compares first evaluation results of the individual imaging units obtained as results of the evaluation in step S330 so as to evaluate reliability.

Specifically, as a method for determining one scanner position in the candidates of a scanner position (a sampling reference position), the maximum value of the correlation peak of each imaging unit calculated in step S330 of the confocal image and that of the nonconfocal image are compared with each other, and a height of a peak value may be determined as a magnitude (reliability) of the correlation at a time of position shift compensation. As another example, the reliability may be determined from a magnitude of a result of comparison between a ratio of the maximum value of the correlation peak to the second largest value calculated for each imaging unit in step S330. As a further example, the reliability may be determined after an error correction process of excepting, among positions of correlation peaks, positions of correlation peaks which are larger than the range (a range taking the maximum shift amount into consideration, for example) of the shift amount of the sampling reference position estimated by a hardware configuration including the resonant scanner. Various methods may be employed as the method for comparing reliability of the correlation in addition to the method employed in this embodiment. Information on the scanner position (the sampling reference position) determined in this step is transmitted from the parameter calculation processor 141 and stored in the storage unit 130 through the controller 120.

Step S350

Subsequently, in step S350, the image construction unit 142 assembles image data to construct an image of the retina of the eye to be inspected based on the sampling data strings of the reciprocating scanning described above for individual imaging units in accordance with the sampling reference positions determined in step S340. Specifically, the image construction unit 142 assembles confocal image data and nonconfocal image data by performing sine compensation for two lines of the image corresponding to one reciprocating scanning operation of the resonant scanner. The construction of the image data is performed to address image distortion by performing weighting on the number of samplings of each pixel by approximating a scanning trajectory of the resonant scanner to a sine wave since an image is distorted when data is uniformly divided into positions in a direction of the axis of ordinates due to inconstant scanning speed of the resonant scanner. The image construction unit 142 stores the constructed image data in the storage unit 130 through the controller 120.

Figure 7:
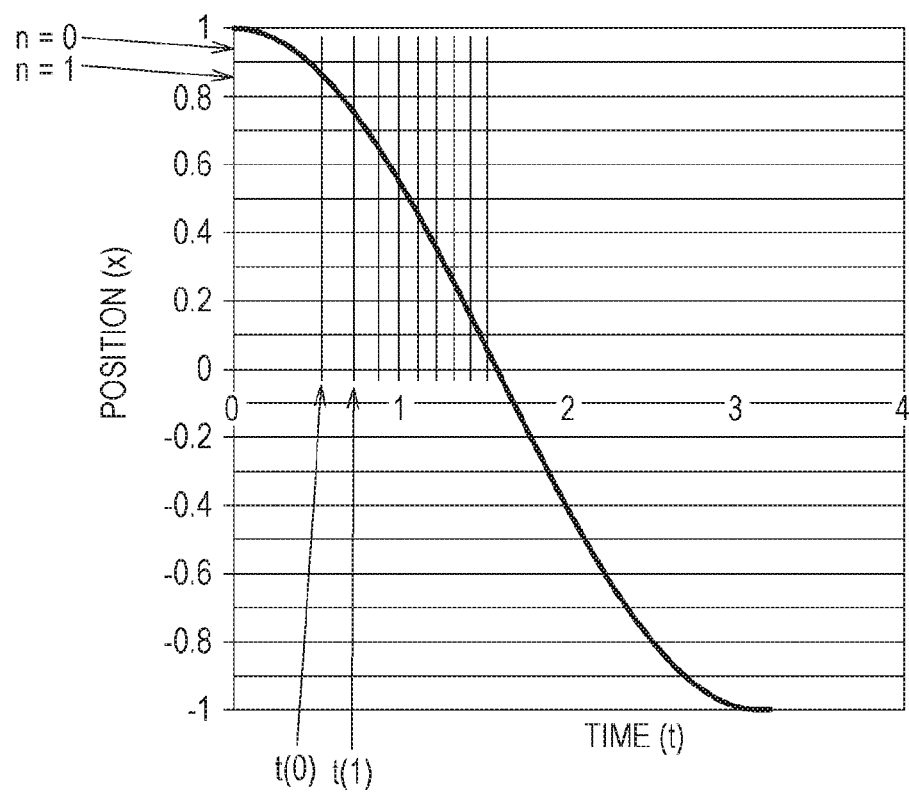
FIG. 7 is a diagram illustrating sine compensation performed when an image construction process in step S350 of FIG. 3 is performed.

FIG. 7 is a diagram illustrating sine compensation performed when the image construction process in step S350 of FIG. 3 is performed. In FIG. 7, an axis of abscissae indicates a time t, an axis of ordinates indicates a position x, and it is assumed that a scanning trajectory of the resonant scanner corresponds to a sine wave of the frequency of the trigger signal of the resonant scanner obtained in step S310 and amplitude is 1.0. The sine wave of FIG. 7 is divided into 10 sections along the axis of ordinates, and n=0 to n=9 are assigned to the divided sections from a time point 0.0. Furthermore, t(0), t(1), and so on are assigned to time points of intersections between straight lines obtained by the division along the axis of ordinates and the sine wave. Data sampled while the resonant scanner scans the sections obtained by the division along the axis of ordinates is assigned to pixels in corresponding positions. By this, although the sampling is performed in several tens MHz at even time intervals, different periods of time in which the resonant scanner scans the individual sections, that is, the resonant scanner performs the sampling, are required for different pixels. Therefore, in a case where an obtained luminance value of a reflection signal is associated with a pixel value in a corresponding position and a plurality of signals correspond to one pixel, a value of the pixel is obtained as an average value of the plurality of signals. Although the scanning trajectory of the resonant scanner is approximated to the sine wave in this embodiment, the approximating method is not limited to this.

Here, the image construction is performed on individual images which are consecutively captured. Specifically, the process described above is performed on one image corresponding to one trigger signal of the galvanoscanner obtained in step S320 and this operation is repeatedly performed for a several number of images. After the image construction is performed on all images, an image group is generated by integrating the images to be stored in the storage unit 130.

Step S360

Next, in step S360, the output unit 150 outputs image data of the retina obtained in step S350 to the external apparatus 300. By this, an image based on the image data output from the output unit 150, for example, is displayed in the external apparatus 300 for the examiner or the like. Furthermore, the output unit 150 outputs information on the image construction, such as sampling reference positions of individual reciprocating scanning operations of the scanner stored in the storage unit 130 in step S310 to step S340, to the external apparatus 300 (a database, for example).

When the process in step S360 is terminated, the process of the flowchart illustrated in FIG. 3 is terminated.

Note that, in this embodiment, the evaluation in step S330 of FIG. 3 may be performed on individual 1D sampling data strings corresponding to a forward scanning and a backward scanning which are adjacent to each other or may be performed on individual 2D sampling data strings corresponding to a plurality of reciprocating scanning operations.

According to this embodiment, image in which distortion thereof caused by characteristics of a scanner is compensated without using a special hardware configuration, a chart image for compensation, or the like may be obtained.

Other Embodiments

In the foregoing embodiment of the present invention, a position of the resonant scanner at a time when a trigger signal is output is estimated every two lines of an image corresponding to reciprocating scanning of the resonant scanner. This is because the adaptive optics SLO apparatus 200 has high transverse resolution, and therefore, a small error of the scanner position caused by a scanner frequency and a time delay of an electric circuit system causes uneven image distortion in individual reciprocating scanning operations. This is further because variation of the scanning of the resonant scanner is affected by temperature in a body of the adaptive optics SLO apparatus 200, instability of a power source, and the like, and therefore, variation of an error of the scanner position is large. The image distortion may appear in a certain cycle depending on a setting of the scanner of the adaptive optics SLO apparatus 200, an imaging condition of an obtained image, or a used scanner (such as a polygonal mirror) other than the resonance scanner. In this case, the number of estimation steps may be reduced by estimating the scanner positions in individual reciprocating scanning operations corresponding to the number of cycles in which image distortion appears.

The estimation of the scanner position may not be performed for one reciprocating scanning line but may be simultaneously performed on a plurality of reciprocating scanning lines. Specifically, a plurality of forward scanning lines and backward scanning lines are set as 2D images, and comparison between spatial frequency domains by 2D FFT is performed so that a positional shift in a scanning direction is calculated. By this method, a uniform sampling reference position may be calculated at once.

Furthermore, although the case where the sampling reference position is automatically determined from among the candidates of the sampling reference position (the scanner position) in step S340 of FIG. 3 is described as an example in the embodiment of the present invention described above, the present invention is not limited to this. For example, the image construction unit 142 may assemble image data using sampling reference positions of sampling reference position candidates, and the image data is displayed in the external apparatus 300, that is, a display apparatus, through the output unit 150. Then, in step S340, the parameter calculation processor 141 may perform the evaluation described above based on an image selected by a user from among images displayed in the external apparatus 300, that is, the display apparatus, so as to determine sampling reference positions (scanner positions). In this case, a parameter to be referred to when the maximum value of the correlation peak is determined may be displayed with the image, or only scanner positions having reliability equal to or smaller than a threshold value may be selected by the user.

Furthermore, improvement of image quality of an image to be displayed and improvement of accuracy of image calculation are expected when an image in which distortion is compensated is used, and therefore, the compensation of distortion of an image of the foregoing embodiment which is executed immediately after imaging in a quick manner may be realized by a hardware configuration and parallel calculation. For example, a multicore calculator, such as an arbitrary FPGA or a GPU, or the like is additionally provided and the calculation to be performed by the image generation unit 140 may be performed by a pipeline process for a plurality of reciprocating scanning operations in parallel.

Moreover, although the retina (the fundus Er) of the eye to be inspected E is employed as the certain region of the eye to be inspected to be subjected to the reciprocating scanning performed by the scanner in the foregoing embodiment of the present invention, the present invention is not limited to this and other portions of the eye to be inspected E may be employed.

Certain aspects of the embodiment(s) of the present invention can be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-125887, filed Jun. 23, 2015 which is hereby incorporated by reference herein in its entirety.

What is claimed is:

1. An image generation apparatus connected to an ophthalmic apparatus including a plurality of imaging units each of which has a photoelectric conversion unit which receives return light of measurement light used by a scanner to scan a region of an eye to be inspected and converts the return light into an electric signal, the image generation apparatus comprising:
an extraction unit configured to extract a reference signal of the scanner obtained while the scanner performs reciprocating scanning once;
a data string generation unit configured to generate sampling data strings of reciprocating scanning based on the electric signals for individual imaging units using the reference signal as a sampling reference position;
a first evaluation unit configured to compare, among the sampling data strings of the reciprocating scanning, a sampling data string of forward scanning with a sampling data string of backward scanning so as to evaluate the correlation between the sampling data strings;
a second evaluation unit configured to compare first evaluation results of the individual imaging units obtained as results of the evaluation performed by the first evaluation unit so as to evaluate reliability;
a reference position compensation unit configured to compensate the sampling reference position in accordance with the first evaluation results and a second evaluation result obtained as a result of the evaluation performed by the second evaluation unit; and
an image construction unit configured to assemble image data to construct an image of the region of the eye based on the sampling data strings of the reciprocating scanning for each imaging unit in accordance with the sampling reference position compensated by the reference position compensation unit.

2. The image generation apparatus according to claim 1, wherein the ophthalmic apparatus further includes an adaptive optics system which compensates aberration of the measurement light and/or the return light occurred in the eye.

3. The image generation apparatus according to claim 1, further comprising a compensation control unit configured to control compensation of an imaging position by tracking a movement of the eye.

4. The image generation apparatus according to claim 1, wherein the first evaluation unit performs the evaluation on a range in which at least change of luminance gradient is large in the sampling data string of the forward scanning and the sampling data string of the backward scanning.

5. The image generation apparatus according to claim 1, wherein the first evaluation unit performs the evaluation using spatial frequency domains of the sampling data string of the forward scanning and the sampling data string of the backward scanning for each imaging unit, and the spatial frequency domains are calculated using discrete Fourier transform.

6. The image generation apparatus according to claim 1, wherein the first evaluation unit performs the evaluation using spatial frequency domains of the sampling data string of the forward scanning and the sampling data string of the backward scanning for each imaging unit, and the spatial frequency domains are calculated using fast Fourier transform.

7. The image generation apparatus according to claim 1, wherein the first evaluation unit performs the evaluation on individual 1D sampling data strings corresponding to the forward scanning and the backward scanning which are adjacent to each other.

8. The image generation apparatus according to claim 1, wherein the first evaluation unit performs the evaluation on individual 2D sampling data strings corresponding to a plurality of reciprocating scanning operations.

9. The image generation apparatus according to claim 1, wherein the first evaluation unit performs the evaluation using a cross correlation method.

10. The image generation apparatus according to claim 1, wherein the first evaluation unit performs the evaluation using a phase-only-correlation method.

11. The image generation apparatus according to claim 1, wherein the first evaluation unit performs the evaluation by performing pattern matching.

12. The image generation apparatus according to claim 9, wherein the first evaluation unit retrieves a maximum value of a correlation peak according to the cross correlation method.

13. The image generation apparatus according to claim 10, wherein the first evaluation unit retrieves a maximum value of a correlation peak according to the phase-only-correlation method.

14. The image generation apparatus according to claim 9, wherein the first evaluation unit determines a position of a correlation peak by arbitrary fitting in the vicinity of a maximum value of the correlation peak according to the cross correlation method.

15. The image generation apparatus according to claim 10, wherein the first evaluation unit determines a position of a correlation peak by arbitrary fitting in the vicinity of a maximum value of the correlation peak according to the phase-only-correlation method.

16. The image generation apparatus according to claim 12, wherein the second evaluation unit compares the maximum values of the correlation peaks of the individual imaging units so as to perform the evaluation.

17. The image generation apparatus according to claim 12, wherein the second evaluation unit performs an error correction process of excepting positions of the correlation peak which are larger than a range of a shift amount of the sampling reference position estimated by a hardware configuration including the scanner among positions of the correlation peak.

18. The image generation apparatus according to claim 1, wherein the plurality of imaging units detect a confocal light beam and at least one nonconfocal light beam.

19. An image generation method of an ophthalmic apparatus including a plurality of imaging units each of which has a photoelectric conversion unit which receives return light of measurement light used by a scanner to scan a region of an eye to be inspected and converts the return light into an electric signal, the image generation method comprising:

extracting a reference signal of the scanner obtained while the scanner performs reciprocating scanning once;

generating sampling data strings of reciprocating scanning based on the electric signals for individual imaging units using the reference signal as a sampling reference position;

comparing, among the sampling data strings of reciprocating scanning, a sampling data string of forward scanning with a sampling data string of backward scanning so as to evaluate the correlation between the sampling data strings;

comparing first evaluation results of the individual imaging units obtained as results of the evaluation so as to evaluate reliability;

compensating the sampling reference position in accordance with the first evaluation results and a second evaluation result obtained as a result of the evaluation of reliability; and assembling image data to construct an image of the region of the eye based on the sampling data strings of the reciprocating scanning for each imaging unit in accordance with the compensated sampling reference position.

20. A non-transitory computer-readable storage medium which stores a program for executing the image generation method set forth in claim 19 by a computer.

* * * * *